US009308359B2

(12) United States Patent
Ward

(10) Patent No.: US 9,308,359 B2
(45) Date of Patent: Apr. 12, 2016

(54) PULL-THROUGH MEDICAL DEVICE

(75) Inventor: Tim Ward, Springville, IN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2555 days.

(21) Appl. No.: 11/136,500

(22) Filed: May 25, 2005

(65) Prior Publication Data
US 2006/0271202 A1    Nov. 30, 2006

(51) Int. Cl.
A61F 2/04       (2013.01)
A61M 27/00    (2006.01)
(Continued)

(52) U.S. Cl.
CPC ........ *A61M 27/008* (2013.01); *A61F 2002/048* (2013.01); *A61F 2002/9505* (2013.01);
(Continued)

(58) Field of Classification Search
CPC ........... A61F 2/042; A61F 2/95; A61F 2/966; A61F 2002/048; A61F 2002/9505; A61M 27/008; A61M 25/0102; A61M 2025/09125; A61M 2025/0024; A61M 2025/0035; A61M 25/0074; A61M 2025/0096; A61M 2025/0161
USPC ............. 623/1.1, 1.11, 1.12, 1.15, 1.16, 1.23, 623/23.66, 23.7, 23.64; 600/585; 604/164.13
See application file for complete search history.

(56) References Cited

U.S. PATENT DOCUMENTS 4,955,858 A * 9/1990 Drews ................................ 604/8
4,963,129 A   10/1990 Rusch
(Continued)

FOREIGN PATENT DOCUMENTS

DE    3816906 A1    11/1989
DE    3900738 A1     7/1990
(Continued)

OTHER PUBLICATIONS https://www.google.com/patents/DE4338320A1?cl=en &dq=DE4338320&hl=en&sa=X &ei=wbvmVICsKeLCsATpz4CoDQ&ved=0 CB0Q6AEwAA 5 pages, google patents translation of DE4338320A1 (cited in IDS).*
(Continued)

*Primary Examiner* — Thomas J Sweet
*Assistant Examiner* — Cheryl Miller
(74) *Attorney, Agent, or Firm* — Kacvinsky Daisak Bluni PLLC

(57) ABSTRACT

A ureteral stent assembly includes a ureteral stent having a distal end portion, a proximal end portion, and a medial end portion. The ureteral stent assembly also includes an elongate positioner for positioning the ureteral stent within the body of the patient. The positioner includes a distal end portion, a proximal end portion, and a medial end portion. A coupling mechanism configured to removably or releasably couple the ureteral stent to the elongate positioner is located on at least one of the distal end portion of the ureteral stent, the medial portion of the ureteral stent, the distal end portion of the positioner, and the medial portion of the positioner. In one embodiment, the ureteral stent includes a lumen that is configured to receive the positioner, and the positioner includes a lumen that is configured to receive a guidewire. In such an embodiment, the guidewire is configured such that when the positioner is disposed within the lumen of the ureteral stent and the guidewire is disposed within the lumen of the positioner, the coupling mechanism is actuated to removably or releasably couple the positioner to the ureteral stent. In one embodiment, the coupling mechanism is a two portion coupling mechanism. In such an embodiment, one portion of the coupling mechanism is located on each of the ureteral stent and the elongate positioner.

21 Claims, 10 Drawing Sheets

(51) Int. Cl.
  *A61M 25/01* (2006.01)
  *A61M 25/09* (2006.01)
  *A61F 2/95* (2013.01)
  *A61M 25/00* (2006.01)

(52) U.S. Cl.
  CPC .......... *A61M25/007* (2013.01); *A61M 25/0045* (2013.01); *A61M 25/0102* (2013.01); *A61M 25/0105* (2013.01); *A61M 25/09* (2013.01); *A61M 2025/09125* (2013.01)

(56) References Cited

U.S. PATENT DOCUMENTS

| | | | | |
|---|---|---|---|---|
| 5,074,849 | A * | 12/1991 | Sachse | 604/540 |
| 5,334,185 | A * | 8/1994 | Giesy et al. | 604/170.01 |
| 5,407,435 | A * | 4/1995 | Sachse | 604/170.01 |
| 5,954,729 | A * | 9/1999 | Bachmann et al. | 606/108 |
| 6,187,013 | B1 * | 2/2001 | Stoltze et al. | 606/108 |
| 6,214,036 | B1 * | 4/2001 | Letendre et al. | 623/1.11 |
| 6,395,021 | B1 * | 5/2002 | Hart et al. | 623/1.15 |
| 6,468,298 | B1 * | 10/2002 | Pelton | 623/1.11 |
| 6,685,735 | B1 * | 2/2004 | Ahari | 623/1.11 |
| 6,821,291 | B2 * | 11/2004 | Bolea et al. | 623/1.11 |
| 6,887,215 | B2 * | 5/2005 | McWeeney | 604/9 |
| 6,908,447 | B2 * | 6/2005 | McWeeney et al. | 604/9 |
| 6,921,378 | B2 * | 7/2005 | O'Keefe et al. | 604/9 |
| 6,939,361 | B1 * | 9/2005 | Kleshinski | 606/200 |
| 7,473,271 | B2 * | 1/2009 | Gunderson | 623/1.12 |
| 7,481,793 | B2 * | 1/2009 | Abrams et al. | 604/164.01 |
| 2002/0123739 | A1 * | 9/2002 | Haacke et al. | 604/544 |
| 2003/0171708 | A1 * | 9/2003 | Segura et al. | 604/8 |
| 2003/0176831 | A1 * | 9/2003 | Gellman et al. | 604/8 |
| 2003/0195456 | A1 * | 10/2003 | Robertson | 604/8 |
| 2003/0199986 | A1 * | 10/2003 | McWeeney et al. | 623/23.7 |
| 2005/0049608 | A1 * | 3/2005 | Aznoian et al. | 606/108 |
| 2005/0085892 | A1 * | 4/2005 | Goto et al. | 623/1.12 |
| 2005/0137448 | A1 * | 6/2005 | Wingler et al. | 600/34 |
| 2005/0273078 | A1 * | 12/2005 | Whitmore et al. | 604/544 |
| 2006/0020326 | A9 * | 1/2006 | Bolduc et al. | 623/1.23 |
| 2006/0190070 | A1 * | 8/2006 | Dieck et al. | 623/1.12 |
| 2007/0043419 | A1 * | 2/2007 | Nikolchev et al. | 623/1.11 |
| 2014/0067041 | A1 * | 3/2014 | Ben-Muvhar et al. | 623/1.15 |

FOREIGN PATENT DOCUMENTS

| | | |
|---|---|---|
| DE | 4338320 A1 | 5/1995 |
| EP | 0516189 A1 | 12/1992 |
| WO | WO 99/58083 A1 | 11/1999 |

OTHER PUBLICATIONS

International Search Report dated Jul. 28, 2006, for International Application No. PCT/US2006/009285, 6 pages.

* cited by examiner

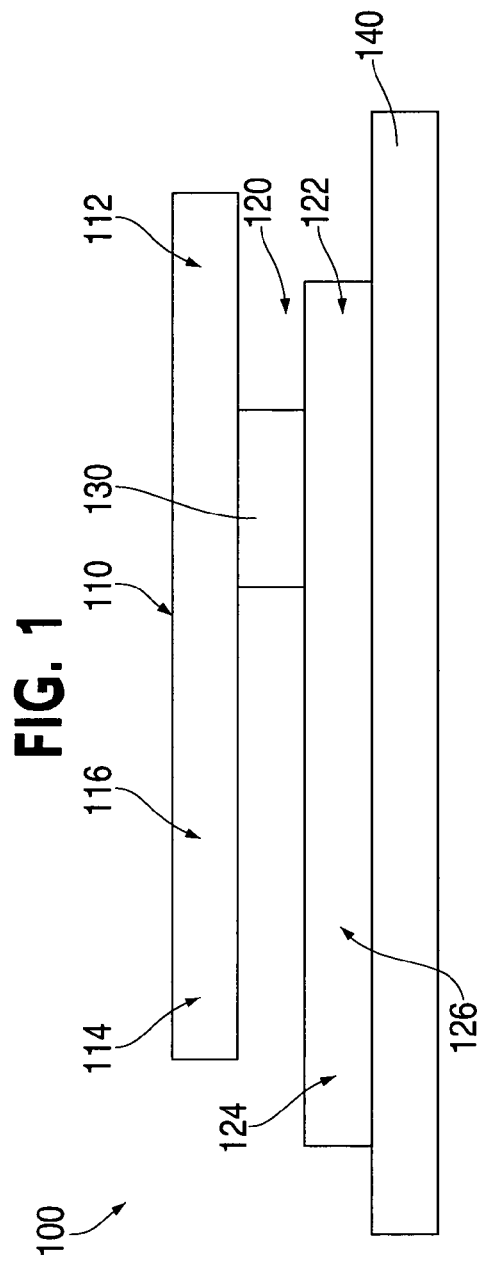
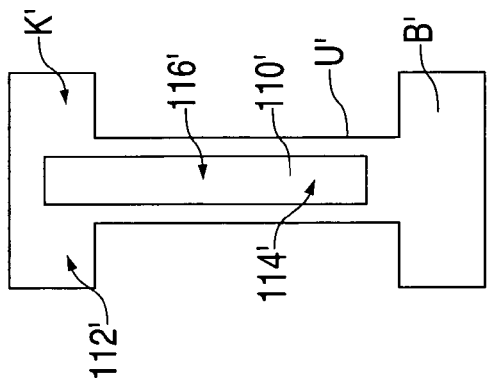
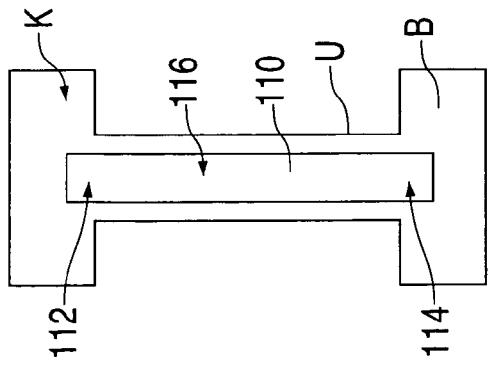

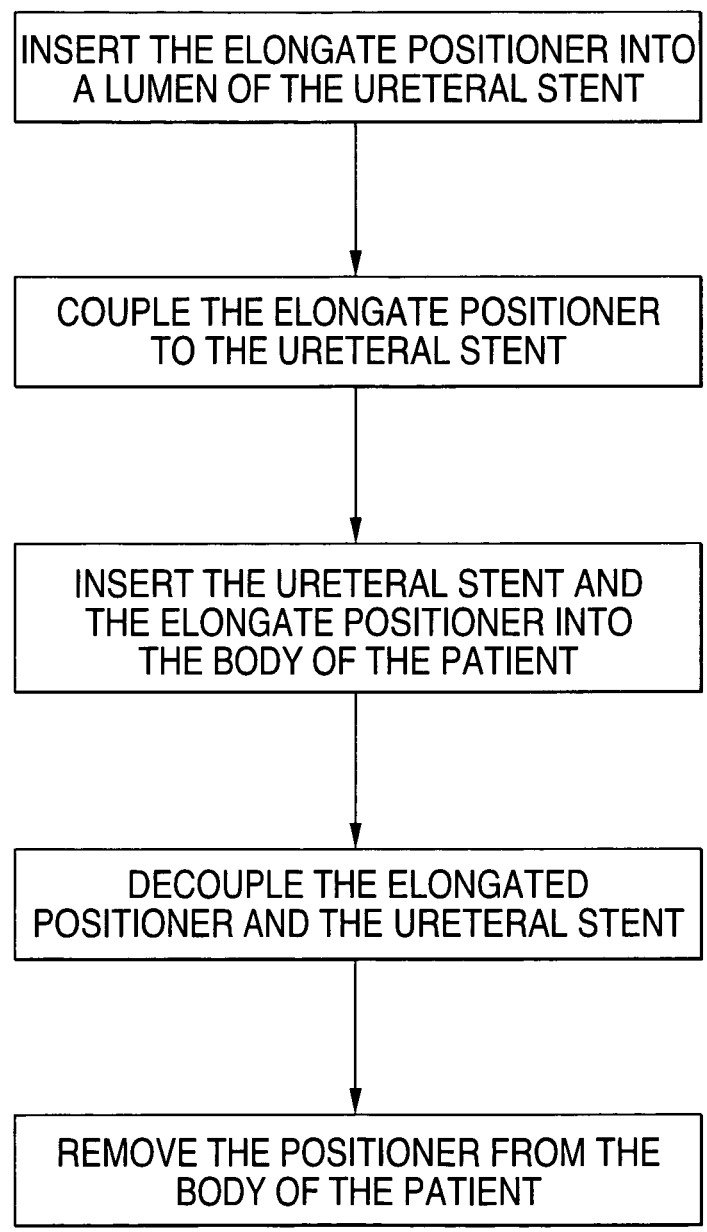

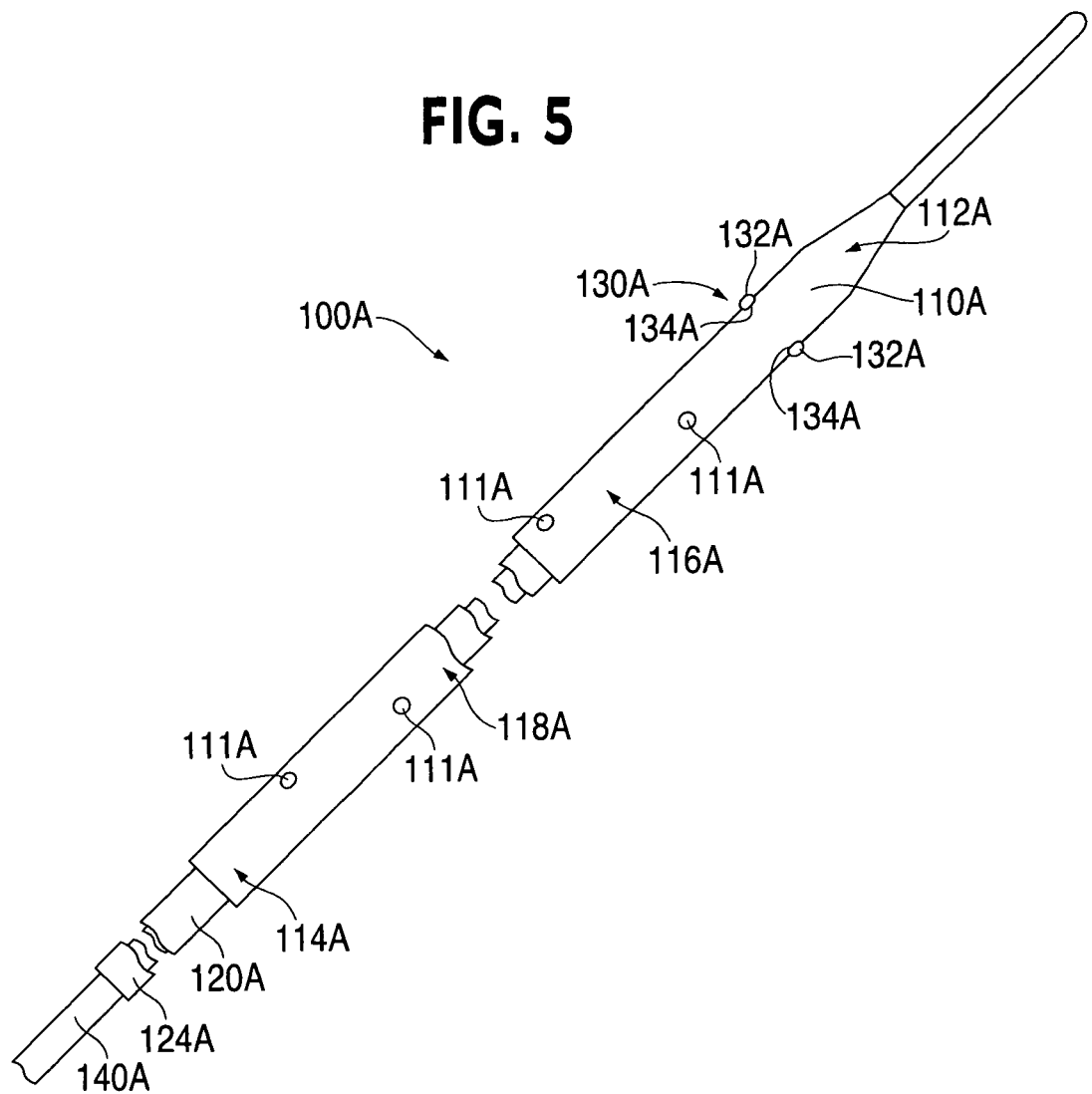

PULL-THROUGH MEDICAL DEVICE

BACKGROUND

The present invention relates generally to a medical device assembly and more particularly to a system and method for placing a ureteral stent.

Ureteral stents are typically placed within a cavity of a patient such that one portion of the ureteral stent is located in a kidney of the patient and another portion of the ureteral stent is located in a bladder of the patient. This is typically achieved by placing a guidewire within the patient, sliding the ureteral stent on the guidewire, and then using a push rod to force the ureteral stent along the guidewire into a desired position within the patient.

Ureteral stents often cause discomfort and pain to the patient once the ureteral stents are positioned within the body. Using soft ureteral stents can reduce the amount of discomfort and pain caused by the implanted ureteral stents but, with conventional placement methods, the stent must be sufficiently rigid such that it can be forced or pushed along the guidewire during implantation without bending or buckling. Thus, there is a need for new methods and devices for placing soft or otherwise flexible ureteral stents.

SUMMARY OF THE INVENTION

A ureteral stent assembly comprises a ureteral stent having a distal end portion for placement in a kidney of a patient, a proximal end portion opposite the distal end portion for placement in a ureter, a bladder, or outside of the body of the patient, and a medial portion located between the distal end portion and the proximal end portion. The ureteral stent assembly also has an elongate positioner for positioning the ureteral stent in a ureteral canal. The elongate positioner has a distal end portion for insertion into the kidney or the ureter of the patient, a proximal end portion for placement outside of the body of the patient, and a medial portion located between the distal end portion of the elongate positioner and the proximal end portion of the positioner. The ureteral stent has a lumen configured to receive the elongate positioner. The ureteral stent assembly also includes a coupling mechanism configured to releasably couple the elongate positioner and the ureteral stent. A portion of the coupling mechanism is located on the distal end portion of the ureteral stent, the medial portion of the ureteral stent, the distal end portion of the elongate positioner, or the medial portion of the elongate positioner.

In one embodiment of the ureteral stent assembly, the elongate positioner has a lumen extending from the distal end portion of the elongate positioner to the proximal end portion of the elongate positioner. The elongate positioner has a projection that defines a portion of the coupling mechanism. The projection has an extended configuration and a retracted configuration. The ureteral stent has a receiver that defines a portion of the coupling mechanism and that is configured to receive the projection of the elongate positioner when the projection is in the extended configuration. In one embodiment, the receiver is an opening defined by the ureteral stent.

In another embodiment, the ureteral stent assembly includes a guidewire that is configured to extend within the lumen of the elongate positioner. The projection of the elongate positioner is configured to be placed in its extended configuration when a portion of the guidewire is disposed within a portion of the lumen of the elongate positioner.

A ureteral stent comprises an elongate member that has a distal end portion configured for placement within a kidney of a patient, a proximal end portion opposite the distal end portion and configured for placement within a bladder or a ureter, and a medial portion located between the distal end portion and the proximal end portion. The elongate member has a mechanism for releasably coupling a positioner to the elongate member. The mechanism includes a coupler disposed on the distal end portion of the elongate member or the medial portion of the elongate member.

A method of placing a ureteral stent within a body includes inserting an elongate positioner into a lumen of the ureteral stent; coupling a coupling portion of the positioner to a coupling portion of the ureteral stent, the coupling portion of the ureteral stent is disposed on a distal end portion of the ureteral stent or a medial portion of the ureteral stent; inserting the positioner and the ureteral stent into the body; decoupling the coupling portion of the positioner and the coupling portion of the ureteral stent; and removing the positioner from the body.

A ureteral stent assembly includes a ureteral stent having a distal end portion, a proximal end portion, and a medial end portion. The ureteral stent assembly also includes an elongate positioner for positioning the ureteral stent within the body of the patient. The positioner includes a distal end portion, a proximal end portion, and a medial end portion. A coupling mechanism configured to releasably couple the ureteral stent to the elongate positioner is located on at least one of the distal end portion of the ureteral stent, the medial portion of the ureteral stent, the distal end portion of the positioner, and the medial portion of the positioner. In one embodiment, the ureteral stent includes a lumen that is configured to receive the positioner, and the positioner includes a lumen that is configured to receive a guidewire. In such an embodiment, the guidewire is configured such that when the positioner is disposed within the lumen of the ureteral stent and the guidewire is disposed within the lumen of the positioner, the coupling mechanism is actuated to releasable couple the positioner to the ureteral stent. In one embodiment, the coupling mechanism is a two portion coupling mechanism. In such an embodiment, one portion of the coupling mechanism is located on each of the ureteral stent and the elongate positioner.

BRIEF DESCRIPTION OF THE DRAWINGS

The present invention is described with reference to the accompanying drawings. In the drawings, like reference numbers indicate identical or functionally similar elements. For example item 110 is identical or functionally similar to item 110A. Similarly, item 110 is identical or functionally similar to item 110'.

FIG. 1 is a schematic illustration of a generic embodiment of a ureteral stent assembly in accordance with the invention.

FIG. 2 is a schematic illustration of a generic embodiment of a ureteral stent in accordance with the invention.

FIG. 3 is a schematic illustration of another generic embodiment of a ureteral stent in accordance with the invention.

FIG. 3A is a flow chart of a method of placing a ureteral stent within a body in accordance with the invention.

FIG. 5 is a partial breakaway view of the ureteral stent assembly of FIG. 4.

DETAILED DESCRIPTION

Figure 4:
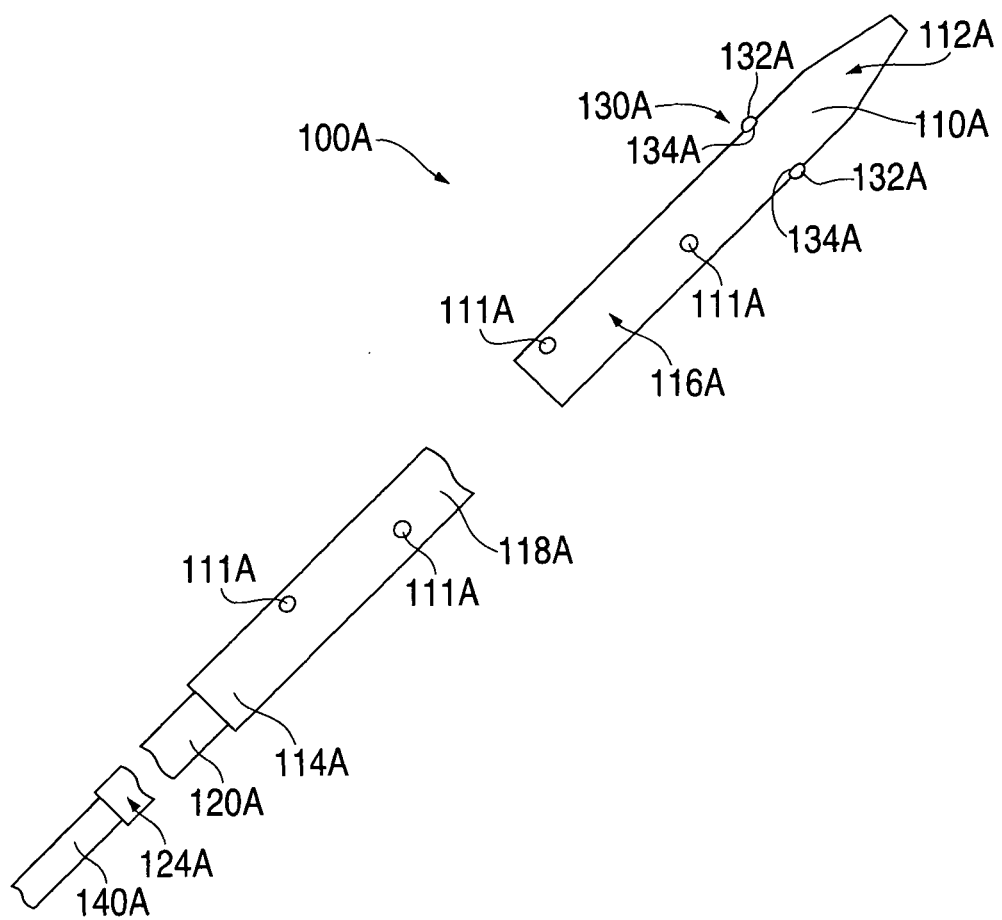
FIG. 4 is a perspective view of an embodiment of a ureteral stent assembly according to the invention.

FIG. 1 is a schematic illustration of a generic embodiment of a ureteral stent assembly 100. The ureteral stent assembly 100 includes a ureteral stent 110, a positioner 120, and a coupling mechanism 130 that is configured to releasably or removably couple the ureteral stent 110 to the positioner 120.

The ureteral stent 110 is an elongate member and is configured to be placed or otherwise implanted into a bodily cavity of a patient. The ureteral stent 110 is configured to facilitate or help facilitate the movement of fluid within a urinary tract of a patient. In one embodiment, as schematically illustrated in FIG. 2, the ureteral stent 110 is configured to be implanted into a body of a patient such that the ureteral stent 10 extends through ureter U from a kidney K of the patient to a bladder B of the patient. In such an embodiment, the ureteral stent 110 includes a distal end portion 112, a proximal end portion 114, and a medial portion 116. The distal end portion 112 is configured to be placed and retained in a kidney K of a patient. The proximal end portion 114 is opposite the distal end portion 112 and is configured to be placed and retained in a bladder B of a patient. The medial portion 116 is located between the distal end portion 112 and the proximal end portion 114. In one embodiment, the ureteral stent 110 may be implanted into the urinary tract of the patient by inserting the stent 110 into the patient transuretherally. In another embodiment, the ureteral stent 110 may be implanted into the urinary tract of the patient by inserting the stent 110 into the patient transdermally or percutaneously.

In another embodiment, as schematically illustrated in FIG. 3, the ureteral stent 110' is configured to be implanted into a body of a patient such that the ureteral stent 110' extends from a kidney K' of the patient to a ureter U' of the patient. In such an embodiment, a distal end portion 112' of the ureteral stent 110' is configured to be placed and retained within the kidney K' of the patient, and a proximal end portion 114' of the ureteral stent 110' is configured to be placed in the ureter U' of the patient. A medial portion 116' is located between the distal end portion 112' and the proximal end portion 114'.

As used herein, the term ureteral stent encompasses a device that has a first end portion configured to be placed within the body of the patient and a second end configured to be placed outside of the body of the patient. For example, in one embodiment, the ureteral stent is configured to be implanted into a body of a patient such that the ureteral stent extends from a kidney of the patient to a location outside of the body of the patient. In such an embodiment, a distal end portion of the ureteral stent is configured to be placed and retained within the kidney of the patient, and the proximal end portion of the ureteral stent is configured to remain outside of the body of the patient. A medial portion of the ureteral stent is located between the distal end portion and the proximal end portion.

In one embodiment, the ureteral stent 110 is a tubular member and includes a side wall that defines a lumen. In one embodiment, the lumen extends from one end of the ureteral stent 110 to another end of the ureteral stent 110. In another embodiment, the lumen extends from the distal end portion 112 of the ureteral stent 110 to the proximal end portion 114 of the ureteral stent 110. In yet another embodiment, the lumen of the ureteral stent 110 only extends through a portion of the ureteral stent 110.

In one embodiment, the distal end portion 112 of the ureteral stent 110 includes a retention structure that is configured to help prevent migration of the ureteral stent 110 downwardly toward the bladder and to, thereby, help retain at least a portion of the ureteral stent 110 within a kidney of a patient. For example, the distal end portion 112 may include a loop portion, a "J" hook portion, a curled portion, a spiral portion, a pigtail portion, or any other structure that is configured to retain at least a portion of the ureteral stent 110 within the kidney of the patient. In other embodiments, the ureteral stent does not include a retention structure.

Similarly, in one embodiment, the proximal end portion 114 of the ureteral stent 110 includes a retention structure that is configured to help prevent migration of the ureteral stent 110 upwardly toward the kidney of the patient and to, thereby, help retain at least a portion of the ureteral stent 110 within a bladder of the patient. For example, the proximal end portion 114 may include a loop portion, a "J" hook portion, a curled portion, a spiral portion, a pigtail portion, or any other structure that is configured to retain at least a portion of the ureteral stent 110 within the bladder of the patient.

In another embodiment, each of the distal end portion 112 of the ureteral stent 110 and the proximal end portion 114 of the ureteral stent 110 includes a retention structure.

The ureteral stent 110 may be formed from a number of different biocompatible materials. The ureteral stent 110 may consist of one material or may be formed, for example by extrusion, of two or more materials along its length. For example, in one embodiment, the distal end portion 112 of the ureteral stent 110 is formed from a first material having a first durometer and the proximal end portion 114 is formed from a second material, which is softer and/or more flexible than the first material, having a second durometer different than the first durometer. Accordingly, the proximal end portion 114 may be made of a softer or more flexible material than that of the distal end 112 and/or the medial portion 116.

The ureteral stent 110 may be formed from any material or materials known in the art to be used in constructing ureteral stents. One subset of biocompatible materials best suited for the ureteral stent 110 exhibit at least some of the following characteristics: high tensile strength, high retention coil strength, excellent biocompatibility and biodurability, excellent radiopacity or flouroscopic visibility, availability in varying durometers, and a low resistance to passage. For example, in one embodiment, the ureteral stent 110 is formed from a polymeric material.

The positioner 120 of the ureteral stent assembly 100 is an elongate member that is configured to position or place the ureteral stent 110 within the body of the patient. In one embodiment, the positioner 120 is configured to engage a portion of the ureteral stent 110 to allow a force to be applied to the ureteral stent 110 such that the ureteral stent 110 may be placed into a desired position within the body. For example, in one embodiment the positioner 120 is configured to engage the ureteral stent 110 via the coupling mechanism. In another embodiment, an end portion of the positioner 120 engages or otherwise contacts a portion of a surface of the side wall of the ureteral stent 110.

The positioner includes a distal end portion 122, a proximal end portion 124, and a medial portion 126. The distal end portion 122 of the positioner 120 is configured to be inserted into a kidney of a patient. The proximal end portion 124 is opposite the distal end portion 122 and is configured to pass through a bladder of the patient and extend from the patient. The medial portion 126 is located between the distal end portion 122 and the proximal end portion 124.

The positioner 120, in one embodiment, is sized and configured to be received by the lumen of the ureteral stent 110. For example, in one embodiment of the ureteral stent assembly 100, the lumen of the ureteral stent 110 extends from the distal end portion 112 to the proximal end portion 114 and the positioner 120 is configured to extend entirely through the lumen. In another embodiment, the positioner 120 extends through only a portion of the lumen of the ureteral stent 110.

In one embodiment, the positioner 120 has a side wall that defines a lumen. The lumen may extend from one end of the positioner 120 to another end of the positioner 120. In another embodiment, the lumen extends from the distal end portion 122 of the positioner 120 to the proximal end portion 124 of the positioner 120. In a further embodiment, the lumen extends through only a portion of the positioner 120.

The coupling mechanism 130 of the ureteral stent assembly 100 is a device that releasably couples the ureteral stent 110 to the positioner 120. Accordingly, the ureteral stent 110 may be coupled to the positioner 120 and may be decoupled or removed from the positioner 120. In one embodiment, the coupling mechanism 130 is configured such that a force may be transferred from the positioner 120 to the ureteral stent 110 to urge the ureteral stent 110 towards the kidney of the patent and another force may be transferred from the positioner 120 to the ureteral stent 110 to urge the ureteral stent 110 towards the bladder of the patient. In other words, when the positioner 120 is coupled to the ureteral stent 110, the positioner 120 may guide the ureteral stent 110 toward the kidney of the patent or may guide the ureter stent 110 toward the bladder.

The coupling mechanism 130 is located on the distal end portion 112 of the ureteral stent 110, the medial portion 116 of the ureteral stent 110, the distal end portion 122 of the positioner 120, or the medial portion 126 of the positioner 120. In other words, in one embodiment the coupling mechanism 130 is located on the distal end portion 112 of the ureteral stent 110; in another embodiment, the coupling mechanism 130 is located on the medial portion 116 of the ureteral stent 110.

The coupling mechanism 130 may include any structure that will allow the ureteral stent 110 to be releasably coupled to the positioner 120. In one embodiment, the coupling mechanism 130 is a one portion coupling mechanism and is entirely located on one of the distal end portion 112 of the ureteral stent 110, the medial portion 116 of the ureteral stent 110, the distal end portion 122 of the positioner 120, and the medial portion 126 of the positioner 120. For example, in one embodiment, an adhesive located on the distal end portion 122 of the positioner 120 is configured to releasably couple the ureteral stent 110 to the positioner 120.

In another embodiment, the coupling mechanism is not a one portion coupling mechanism. Rather, the coupling mechanism 130 is a two portion coupling mechanism. For example, in one embodiment, a first portion of the coupling mechanism 130 is located on the ureteral stent 110 and a second portion of the coupling mechanism 130 is located on the positioner 120. In one embodiment, a first portion of the coupling mechanism 130 is located on the medial portion of the ureteral stent 110 and a second portion of the coupling mechanism 130 is located on the medial portion of the positioner 120. Accordingly, the first and the second portions of the coupling mechanism 130 cooperate or are connected together to couple the ureteral stent 110 to the positioner 120 and are removed or released from each other to remove or decouple to the ureteral stent 110 from the positioner 120. For example, in one embodiment, the coupling mechanism 130 includes a two portion coupling mechanism or coupler, such as a snap, a male portion and corresponding female portion, hook and loop material, a projection/receiver structure, corresponding or mating threaded portions, or any other two portion coupling mechanism or coupler.

As illustrated in FIG. 1, in one embodiment, the ureteral stent assembly 100 includes a guidewire 140. The guidewire 140 is an elongate member of sufficient stiffness such that it may be maneuvered within a bodily cavity of the patient to position the guidewire within the bodily cavity of the patient. The guidewire 140 may be any conventional guidewire. For example, the guidewire 140 may be a Sensor™ Guidewire, a Glidewire® Guidewire, a Zebra® Urological Guidewire, a Lubriglide™ Coated Guidewire, or a PTFE Coated Guidewire, all as marketed and sold by Boston Scientific.

In one embodiment, the guidewire 140 is sized and configured to be received by the lumen of the positioner 120. For example, in one embodiment, the lumen of the positioner 120 extends from the distal end portion 122 of the positioner 120 to the proximal end portion 124 of the positioner 120, and the guidewire 140 extends entirely through the lumen of the positioner 120. In another embodiment, the guidewire 140 extends through only a portion of the lumen of the positioner 120.

In one embodiment of the ureteral stent assembly 100, when the guidewire 140 is disposed within the lumen of the positioner 120, the coupling mechanism 130 is actuated to releasably couple the positioner 120 to the ureteral stent 110. In contrast, the coupling mechanism 130 is not actuated to couple the positioner 120 to the ureteral stent 110 when the guidewire 140 is not disposed within the lumen of the positioner 120. In other words, the guidewire 140 may be inserted into the lumen of the positioner 120 to couple the positioner 120 to the ureteral stent 110. Additionally, the guidewire 140 may be removed from the lumen of the positioner 120 to remove or decouple the positioner 120 from the ureteral stent 110.

As detailed in FIG. 3A, In one embodiment, the ureteral stent 110 may be placed or otherwise implanted within the body of a patient as follows. The positioner 120 is inserted into the lumen of the ureteral stent 110, and the positioner 120 is coupled to the ureteral stent 110. The positioner 120 and ureteral stent 110 combination is inserted into the body of the patient. For example, in one embodiment, the positioner 120 and ureteral stent 110 combination is forced (by applying a force to the positioner 120) along a guidewire 140 into a desired position within the body of the patient. Specifically, in one embodiment, the coupling mechanism 130 is a two portion coupling mechanism. One portion of the coupling mechanism 130 is located on the distal end portion 122 of the ureteral stent 110 and another portion of the coupling mechanism 130 is located on the distal end portion 122 of the positioner 120. Accordingly, the force applied to the positioner 120 is transferred to the distal end portion 112 of the ureteral stent 110 through the coupling mechanism 130.

Thus, the proximal end portion 114 and the medial portion 116 of the ureteral stent 110 are effectively "pulled" into the desired position within the body of the patient. The positioner 120 is then decoupled or otherwise removed or released from the ureteral stent 110. The positioner 120 is then removed from the body of the patient. Accordingly, the ureteral stent 110 remains within the body of the patient at the desired location.

In another embodiment, the ureteral stent 110 may be placed or otherwise implanted within the body of the patient as follows. Using conventional methods, the guidewire 140 is placed in the body such that one end of the guidewire is disposed within a kidney of the patient, a medial portion of the guidewire extends through a ureter, and another end of the guidewire extends from the body of the patient. The positioner 120 is inserted into the lumen of the ureteral stent 110. The positioner 120 and ureteral stent 110 are then placed onto the guidewire 140 by inserting the guidewire 140 into the lumen of the positioner 120. As the guidewire 140 is placed within the lumen of the positioner 120, the coupling member 130 is actuated or activated to couple the positioner 120 to the ureteral stent 110. The positioner 120 and ureteral stent 110 combination is then pushed or otherwise forced, for example, via the proximal end portion of the positioner 120, along the guidewire 140 into the desired position within the body of the patient.

In another embodiment, the positioner 120 and the ureteral stent 110 are placed onto the guidewire 140 prior to the placement of the guidewire 140 into the body of the patient.

The guidewire 140 is then removed or retracted from the body of the patient. Once the guidewire 140 is moved with respect to the lumen of the positioner 120 past the coupling member 130, the coupling member 130 is deacutated and the positioner 120 is decoupled or otherwise removed or released from the ureteral stent 110. At such time, the positioner 120 may be removed from the lumen of the ureteral stent 110 and from the body of the patient. Accordingly, the ureteral stent 110 remains within the body of the patient at the desired location.

FIGS. 4, 5, 6A, 6B, 7, 10A, 10B, and 11-12 illustrate an embodiment of a ureteral stent assembly 100A. The ureteral stent assembly 100A includes a ureteral stent 110A, a positioner 120A, and a coupling mechanism 130A that is configured to releasably couple the positioner 120A to the ureteral stent 110A.

The ureteral stent 110A is an elongate member and is configured to be placed or otherwise implanted within a body of a patient. The ureteral stent 110A is configured to facilitate or help facilitate the movement of fluid within a urinary tract of a patient. Accordingly, the ureteral stent 110A is configured to extend from a kidney of the patient to a bladder of the patient. The ureteral stent 110A includes a distal end portion 112A, a proximal end portion 114A, and a medial portion 116A. The distal end portion 112A is configured to be placed and retained in a kidney of the patient. The proximal end portion 114A is opposite the distal end portion 112A and is configured to be placed and retained within a bladder of the patient. The medial portion 116A is located between the distal end portion 112A and the proximal end portion 114A.

In another embodiment, the ureteral stent 110A is configured to extend from a kidney of a patient to a ureter of the patient. In yet another embodiment, the ureteral stent 110A is configured to extend from a kidney of a patient to a location outside of the body of the patient.

The ureteral stent 110A is a tubular member and includes a side wall 118A that defines a lumen 119A. In one embodiment, the thickness of the side wall 118A is between about 0.05 mm and 0.35 mm, the diameter of the lumen 119A is between about 0.5 mm and 5 mm, and the outside diameter is between about 1 mm and 4 mm or between 3 French and 12 French. The lumen 119A extends from the distal end portion 112A of the ureteral stent 110A to the proximal end portion 114A of the ureteral stent 110A.

In an another embodiment, the thickness of the side wall 118A of the ureteral stent 110A is larger than 0.35 mm. In another embodiment, the thickness of the side wall 118A of the ureteral stent 110A is less than 0.05 mm. In yet another embodiment, the thickness of the side wall 118A of the ureteral stent 110A varies from one end portion of the ureteral stent 110A to another end portion of the ureteral stent 110A. In another embodiment, the diameter of the lumen 119A is less than 0.5 mm or greater than 5 mm.

In the illustrated embodiment, the ureteral stent 110A includes ports or openings 111A defined by the side wall 118A. The ports or openings 111A defined by the side wall 118A of the ureteral stent 110A provide fluid communication between the exterior of the ureteral stent 110A and the lumen 119A.

Figure 7:
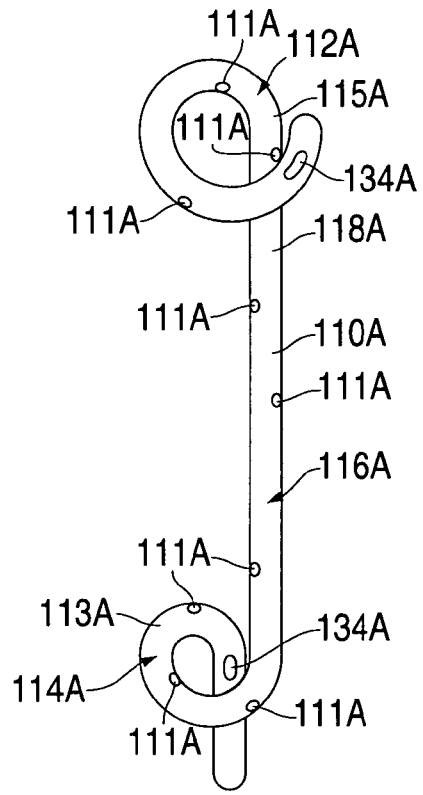
FIG. 7 is a perspective view of a ureteral stent of the ureteral stent assembly of FIG. 4.

As best illustrated in FIG. 7, the distal end portion 112A of the ureteral stent 110A includes a retention structure 115A that is configured to help prevent migration of the ureteral stent 110A downwardly toward the bladder and to, thereby, help retain at least a portion of the ureteral stent 110A within a kidney of the patient. The retention structure 115A includes a loop portion.

Figure 8:
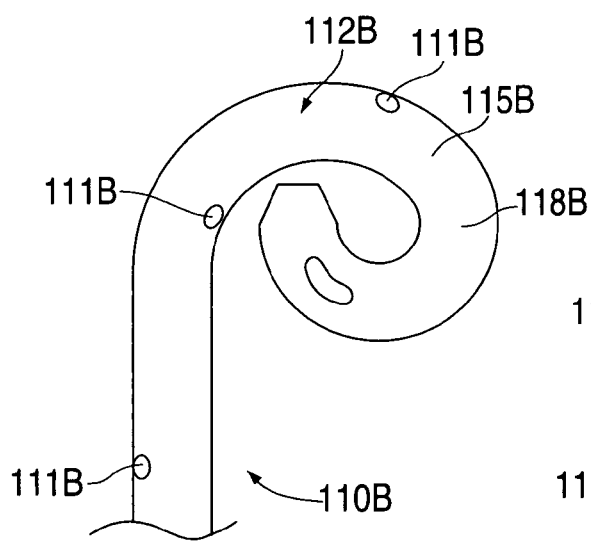
FIGS. 8 and 9 are perspective views of portions of other embodiments of a ureteral stent according to the invention.
Figure 9:
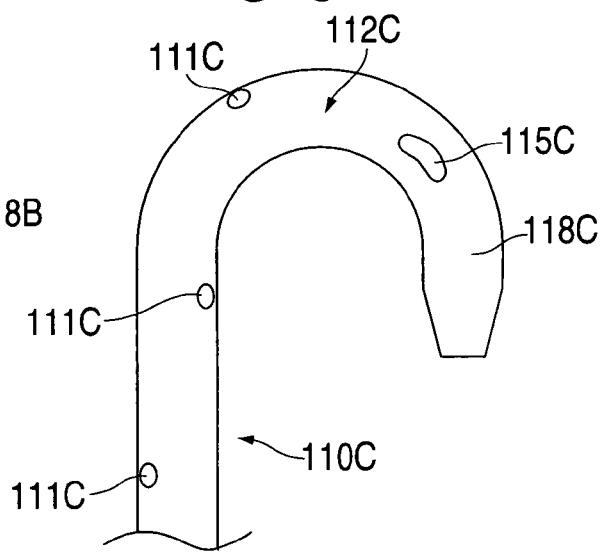

Although the retention structure 115A is illustrated as including a loop portion, it is not necessary that the retention structure 115A have such a shape or configuration. FIGS. 8 and 9 illustrate other embodiments of the distal end portion of the ureteral stent. Accordingly, as illustrated in FIG. 8, in one embodiment, the ureteral stent 110B includes a distal end portion 112B and ports or openings 111B defined by a side wall 118B. The distal end portion 112B has a retention structure 115B that includes a spiral portion. As illustrated in FIG. 9, in yet another embodiment, the ureteral stent 110C includes a distal end portion 112C and ports or openings 111C defined by a side wall 118C. The distal end portion 112C has a retention structure 115C that includes a "J" hook portion or configuration. In further embodiments, the retention structure has another shape or configuration that is configured to help retain at least a portion of the ureteral stent within the kidney of the patient.

Similarly, the proximal end portion 114A of the ureteral stent 110A includes a retention structure 113A that is configured to help prevent migration of the ureteral stent 110A upwardly toward the kidney of the patient. The retention structure 113A includes a loop portion. In other embodiments, the retention structure 113A includes a "J" hook portion, a curled portion, a spiral portion, a pigtail portion, or any other structure that is configured to help retain at least a portion of the ureteral stent 110A within the bladder of the patient.

The ureteral stent 110A is formed from Percuflex® as marketed and sold by Boston Scientific or another polymeric material. In other embodiments, the ureteral stent 110A is formed from a different biocompatible material. In a further embodiment, the ureteral stent 110A is formed of more than one material, for example, by extrusion of two or more materials along the length of the ureteral stent 110A.

As best illustrated in FIGS. 4, 5, 6A, 6B, 10A, 10B, and 11, the positioner 120A of the ureteral stent assembly 100A is an elongate member and is configured to position or place the ureteral stent 110A within a body of a patient. The positioner 120A includes a distal end portion 122A, a proximal end portion 124A, and a medial portion 126A. The distal end portion 122A of the positioner 120A is configured to be inserted into a kidney of a patient. The proximal end portion 124A is opposite the distal end portion 122A and is configured to extend from the body of the patient. The medial portion 126A is located between the distal end portion 122A and the proximal end portion 124A.

The positioner 120A has a side wall 128A that defines a lumen 129A. The lumen 129A extends from the distal end portion 122A of the positioner 120A to the proximal end portion 124A of the positioner 120A. In one embodiment, the positioner is made of a polymeric material.

The positioner 120A is sized and configured to be received by the lumen 119A of the ureteral stent 110A. Specifically, the positioner 120A is configured to extend through a portion of the lumen 119A. When the positioner 120A is disposed with the lumen 119A of the ureteral stent 110A, a distal end 121A of the positioner 120A contacts or otherwise engages a portion of a inner surface 117A of the side wall 118A of the ureteral stent 110A. Accordingly, as will be described in detail below, force may be applied by the positioner 120A to the ureteral stent 110A, via the coupling member 130A and via the engagement between the distal end 121A and the surface 117A, to position the ureteral stent 110A within the body of the patient.

In another embodiment, the distal end of the positioner 120A does not contact or otherwise engage a portion of an inner surface 117A of the side wall 118A of the ureteral stent 110A to apply force to the ureteral stent 110A. In another embodiment, another portion of the positioner 120A contacts or engages the ureteral stent 110A such that force may be applied to the ureteral stent 110A. In yet another embodiment, only the coupling mechanism 130A functions to transfer a force applied to the positioner 120A to the ureteral stent 110A.

The coupling mechanism 130A of the ureteral stent assembly 100A is configured to releasably couple the ureteral stent 110A to the positioner 120A. Accordingly, the ureteral stent 110A may be coupled to the positioner 120A and may be decoupled or removed from the positioner 120A.

The coupling mechanism 130A is a two portion coupling mechanism and includes projections 132A located on the positioner 120A and receivers 134A defined by the side wall 118A of the ureteral stent 110A. Specifically, in the illustrated embodiment, the projections 132A are located on the distal end portion 122A of the positioner 120A. The receivers 134A defined by the side wall 118A of the ureteral stent 110A are located at the distal end portion 112A of the ureteral stent 110A.

In an another embodiment, the projections 132A are located on the medial portion 126A of the positioner 120A. In yet another embodiment, the receivers 134A defined by the side wall 118A of the ureteral stent 110A are located at the medial end portion 116A of the ureteral stent 110A.

The projections 132A are sized and configured to be received by, and removed from, the receivers 134A to removably or releasably couple the ureteral stent 110A to the positioner 120A. Specifically, in the illustrated embodiment, the projections 132A are sized and configured to be snapped or otherwise locked into the receivers 134A to couple the ureteral stent 110A to the positioner 120A. Subsequently, the projections 132A may be removed from the receivers 134A to decouple or otherwise remove the ureteral stent 110A from the positioner 120A.

In the illustrated embodiment, the coupling mechanism 130A includes flexible or bendable portions 136A. The flexible or bendable portions 136A are configured to flex or bend such that the projections move with respect to the side wall 128A of the positioner 120A. As illustrated in FIG. 11, the flexible or bendable portions 136A are located proximally from the projections 132A. In other words, the flexible or bendable portions 136A are located between the proximal end portion 122A of the positioner 120A and the projections 132A. The flexible or bendable portions 136A are biased such that the projections 132A are retained in retracted positions or configurations when an outside force is not acting on the flexible or bendable portion 136A. As best illustrated in FIGS. 10A and 11, the flexible or bendable portions 136A are configured to flex or bend to place the projections 132A in extended positions or configurations.

Figure 10A:
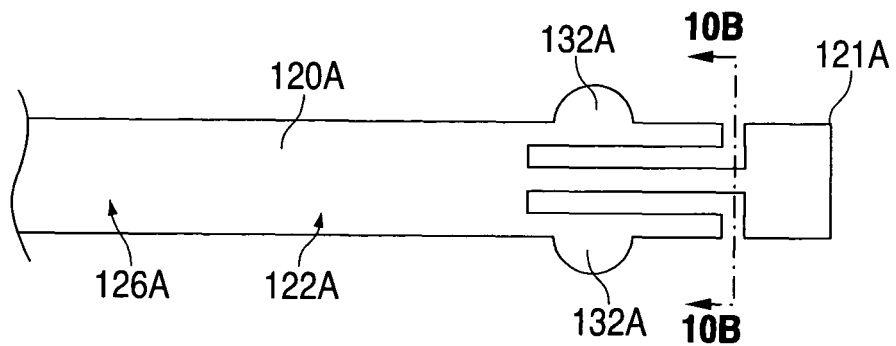
FIG. 10A is a perspective view of a positioner of the ureteral stent assembly of FIG. 4 in a extended configuration.
Figure 10B:
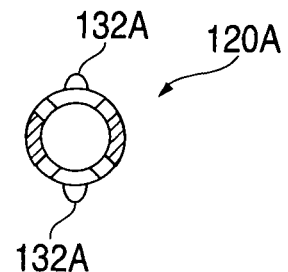
FIG. 10B is a cross-sectional view of the positioner of FIG. 10A taken along line 10B-10B of FIG. 10A.
Figure 11:
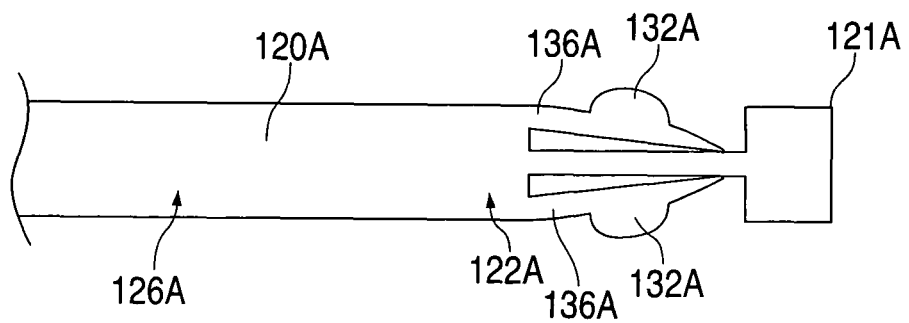
FIG. 11 is a perspective view of a positioner of FIG. 10A in a retracted configuration.
Figure 12:
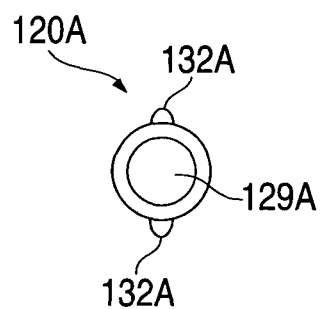
FIG. 12 is an end view of the positioner of FIG. 10A.

FIG. 10B is a cross-sectional view of the positioner 120A taken along line 10B-10B of FIG. 10A. FIG. 12 is an end view of the positioner 120A.

Figure 13:
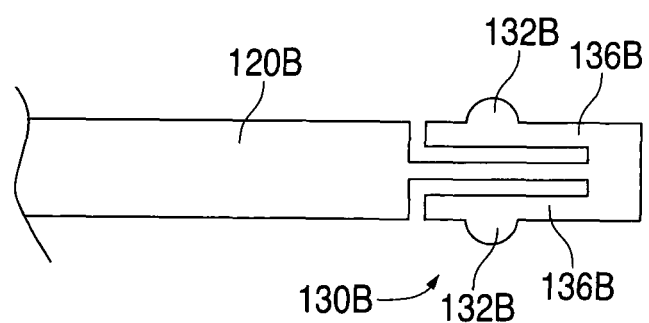
FIG. 13 is a perspective view of another embodiment of a positioner according to the invention.

As illustrated in FIG. 13, in another embodiment, the coupling mechanism 130B includes flexible or bendable portions 136B that are located distally from the projections 132B. In other words, the projections 132B are located between the proximal end portion of the positioner and the flexible or bendable portions 136B.

In another embodiment, the coupling mechanism 130A does not include a flexible or bendable portion. Rather, the coupling mechanism 130A includes a hinge portion, a slideable portion, or any other type of structure that allows the projections 132A to move with respect to the side wall 128A of the positioner 120A from retracted positions or configurations to extended positions or configurations.

Although the receivers 134A are illustrated as being openings defined by the side wall 118A of the ureteral stent 110A, it is not necessary that the receivers 134A be openings. For example, the receivers 134A may be detents or any other types of structures that are configured to removably receive the projections 132A.

In other embodiments, the coupling mechanism 130A is not a two portion coupling mechanism or coupler. Rather, the coupling mechanism 130A is a one portion coupling mechanism and is entirely located on one of the distal end portion 112 of the ureteral stent 110, the medial portion 116 of the ureteral stent 110, the distal end portion 122 of the positioner 120, and the medial portion 126 of the positioner 120. For example, in one embodiment, a projection or more than one projection having an extended configuration and a retracted configuration is located on the positioner 120A and is configured to contact the inner surface 117A of the side wall 118 of the ureteral stent 110A to removably or releasably couple the positioner 120A to the ureteral stent 110A via friction.

Figure 14:
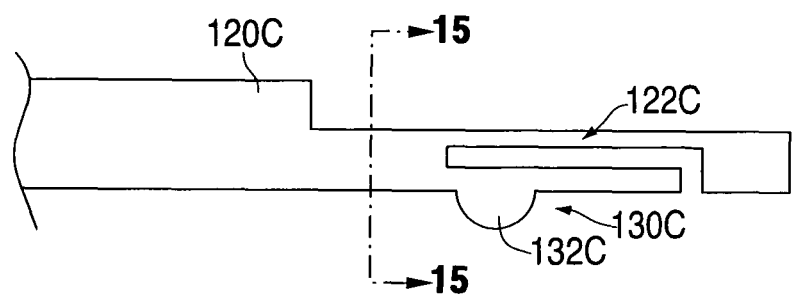
FIG. 14 is a perspective view of another embodiment of a positioner according to the invention.
Figure 15:
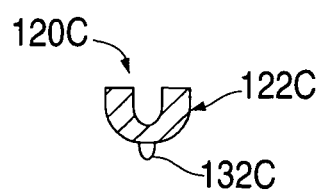
FIG. 15 is a cross-sectional view of the positioner of FIG. 14 taken along line 15-15 of FIG. 14.

As illustrated in FIGS. 14 and 15, in another embodiment, the positioner 120C includes a "U" shaped distal end portion 122C. A coupling mechanism 130C includes a single projection 132C that is located on the distal end portion 122C of the positioner 120C. In such an embodiment, the projection 132C is configured to interact with a receiver or opening defined by the side wall of the ureteral stent to removably or releasably couple the positioner 120C to the ureteral stent.

In the illustrated embodiment, the ureteral stent assembly 100A includes a guidewire 140A. The guidewire 140A is an elongate member of sufficient stiffness such that it may be maneuvered within a bodily cavity of the patient to position the guidewire within the body of the patient. In one embodiment, the guidewire 140A is a conventional guidewire, such as a Sensor™ Guidewire, a Glidewire® Guidewire, a Zebra® Urological Guidewire, a Lubriglide™ Coated Guidewire, or a PTFE Coated Guidewire, all as marketed and sold by Boston Scientific.

In one embodiment, the guidewire 140A is sized and configured to be received by the lumen 129A of the positioner 120A. In the illustrated embodiment, the guidewire 140A extends entirely through the lumen of the positioner 120A. In other embodiments, the guidewire 140A extends through only a portion of the lumen 129A of the positioner 120A.

When the guidewire 140A is disposed within the lumen 129A of the positioner 120A, the coupling mechanism 130A is actuated to couple the positioner 120A to the ureteral stent 110A. In contrast, the coupling mechanism 130A is not actuated to couple the positioner 120A to the ureteral stent 110A when the guidewire 140A is not disposed within the lumen 129A of the positioner 120A.

Figure 6B:
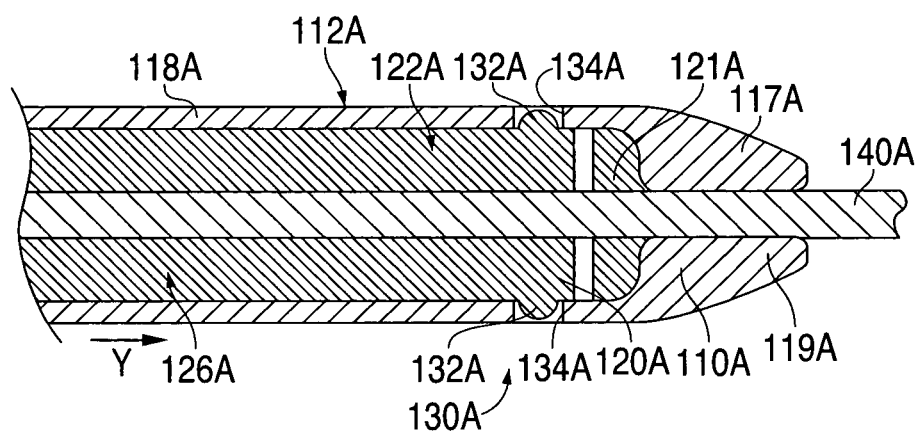
FIG. 6B is a cross-sectional view of the ureteral stent assembly of FIG. 4 taken along line 6B-6B of FIG. 6A.
Figure 6A:
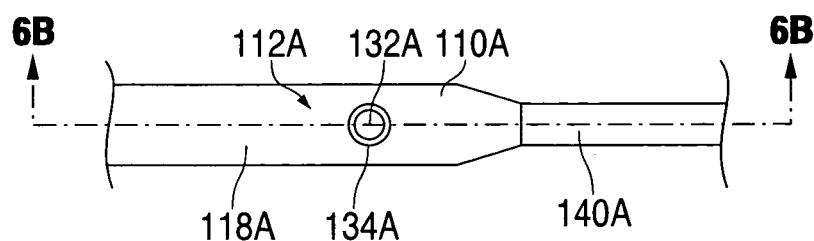
FIG. 6A is a perspective view of a portion of the ureteral stent assembly of FIG. 4.

Specifically, in the illustrated embodiment, the positioner 120A is inserted into the lumen 119A of the ureteral stent 110A, and then the guidewire 140A is inserted into the lumen 129A of the positioner 120A. As best illustrated in FIGS. 6A and 6B, the guidewire 140A contacts and flexes, bends, or otherwise moves the flexible portions 136A of the coupling mechanism 130A to move the projections 132A from their retracted or disengaged positions or configurations to their extended or engaged positions or configurations such that the projections 132A are inserted and retained within the receivers 134A defined by the side wall 118A of the ureteral stent 110A. In contrast, when the guidewire 140A is removed from the lumen 129A of the positioner 120A, the coupling mechanism 130A returns to its retracted position or configuration thereby removing the projections 132A from the receivers 134A.

The ureteral stent 110A may be placed or otherwise implanted within the body of a patient as follows. Using conventional methods, the guidewire 140A is placed in the body such that one end of the guidewire is disposed within a kidney of the patient, the guidewire passes through a ureter of the patient, and another end portion extends from the body of the patient. The positioner 120A is inserted into the lumen 119A of the ureteral stent 110A. Once the positioner 120A is inserted into the lumen 119A of the ureteral stent 110A, the retention structures 113A and 115A are flexed or otherwise bent into a linear shape. The positioner 120A and ureteral stent 110A are then placed onto the guidewire 140A by inserting the guidewire 140A into the lumen 129A of the positioner 120A. As the positioner 120A and ureteral stent 110A are placed onto the guidewire 140A, the coupling member 130A is actuated or moved from its retracted position to its extended position. Accordingly, the projections 132A are inserted into the receivers 134A and the positioner 120A is coupled to the ureteral stent 110A. The positioner 120A and ureteral stent 110A combination can then be pushed or otherwise forced, for example, via a force applied to the proximal end portion 124A of the positioner 120A, along the guidewire 140A into the desired position within the body of the patient. Thus, the proximal end portion 114A and the medial portion 1 16A of the ureteral stent 110A are effectively "pulled" into the desired position within the body of the patient from the distal end portion 112A.

The guidewire 140A can then be removed or retracted from the body of the patient. Once the guidewire 140A is moved with respect to the lumen 129A of the positioner 120A past the coupling member 130A, the force against the coupling member 130A will be removed and the bias of the coupling member 130A will cause the coupling member 130A to move from its extended position to its retracted position. Accordingly, the projections 132A will be removed from the receivers 134A, thereby causing the ureteral stent 110A to be decoupled from the positioner 120A. At such time, the positioner is removed from the lumen 119A of the ureteral stent 110A and from the body of the patient. Accordingly, the retention structures 113A and 115A of the ureteral stent 110A assume their original non-linear configurations and the ureteral stent 110A is retained in its desired position or location within the body of the patient.

Figure 6C:
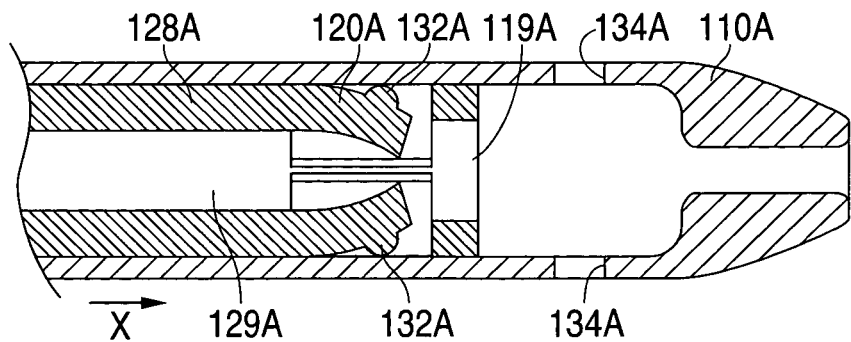
FIGS. 6C-6E are cross-sectional views of the ureteral stent assembly of FIG. 4 at various points in time.
Figure 6D:
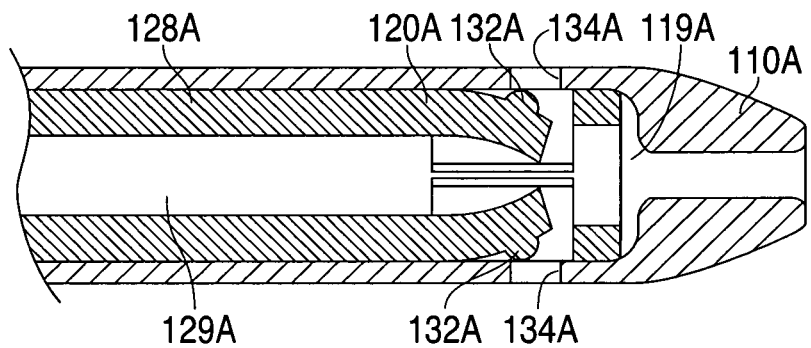
Figure 6E:
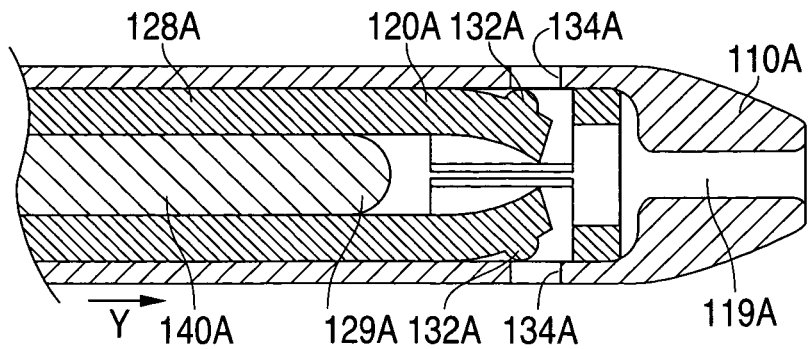

As illustrated in FIGS. 6C-6E, in an another embodiment, the positioner 120A and the ureteral stent 110A are placed onto the guidewire 140A prior to the insertion of the guidewire 140 into the body of the patient. In such an embodiment, the positioner 120A may be inserted into the lumen 119A of the ureteral stent 110A and moved in the direction of arrow X as illustrated in FIGS. 6C and 6D. The guidewire 140A is then inserted into the lumen 129A of the positioner 120A and moved in the direction of arrow Y as illustrated in FIG. 6E. As described in detail above, the guidewire 140A will force the projections 132A into the receivers 134A.

The principles, preferred embodiments, and modes of operation of the present invention have been described in the foregoing description. However, the invention that is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A ureteral stent assembly comprising:
   a ureteral stent having a distal end portion for placement in a kidney of a patient, a proximal end portion opposite the distal end portion, and a medial portion located between the distal end portion and the proximal end portion, the ureteral stent having a sidewall, the sidewall having an inner surface and outer surface, the inner surface of the sidewall defining a lumen between the distal end portion of the ureteral stent and the proximal end portion of the ureteral stent, the sidewall on the distal end portion of the ureteral stent defining an opening that extends from the inner surface to the outer surface,
   the opening defining a first portion of a coupling mechanism, the proximal end portion being configured to be placed in at least one of a ureter of the patient, a bladder of the patient, and outside of a body of the patient, the distal end portion of the ureteral stent having a retention member, the retention member having a first configuration and a second configuration, the retention member being non-linear and configured to help retain the distal end portion of the ureteral stent in place within the kidney of the patient when the retention member is in the second configuration;
   an elongate positioner for positioning the ureteral stent in the ureter, the elongate positioner having a distal end portion for insertion into at least one of the kidney of the patient and the ureter of the patient, a proximal end portion for placement outside of the body of the patient, and a medial portion located between the distal end portion of the elongate positioner and the proximal end portion of the elongate positioner,
   the distal end portion of the elongate positioner having a second portion of the coupling mechanism coupled to the first portion of the coupling mechanism when the elongate positioner is in a first position, at least a portion of the elongate positioner being disposed within the lumen of the ureteral stent when in the first position, the second portion of the coupling mechanism at least partially extending into the opening from the inner surface of the sidewall of the ureteral stent when in the first position, the second portion of the coupling mechanism being disposed within the lumen defined by the ureteral stent and uncoupled from the first portion of the coupling mechanism when the elongate positioner is in a second position, the elongate positioner includes a lumen; and a guidewire for insertion into the lumen of the elongate positioner, the coupling mechanism being configured such that the elongate positioner and the ureteral stent are coupled together in response to the guidewire being inserted into the lumen of the elongate positioner and advanced distally within the lumen of the ureteral stent, the coupling mechanism being configured such that the elongate positioner and the ureteral stent are decoupled in response to the guidewire being removed from the lumen of the elongate positioner by proximal advancement from inside the lumen of the ureteral stent.

2. The assembly of claim 1, wherein the second portion of the coupling mechanism is configured to flex into the opening of the ureteral stent when in the first position.

3. The assembly of claim 1, wherein the elongate positioner includes a sidewall having an inner surface, the inner surface of the sidewall of the elongate positioner defining the lumen of the elongate positioner, the second portion of the coupling mechanism being bendable such that portions of the inner surface of the sidewall of the elongate positioner move towards each other when moving from the first position to the second position.

4. The assembly of claim 1, wherein the second portion of the coupling mechanism includes a deflectable projection, the deflectable projection being at least partially inserted into the opening of the ureteral stent when in the first position.

5. The assembly of claim 1, wherein the second portion of the coupling mechanism is engaged with the first portion of the coupling mechanism when the elongate positioner is in the first position, the second portion of the coupling mechanism being disengaged from the first portion of the coupling mechanism when the elongate positioner is in the second position.

6. The assembly of claim 1, wherein the second portion of the coupling mechanism includes a bendable portion, the bendable portion having a projection that extends away from a sidewall defined by the elongate positioner, the projection being at least partially disposed within the opening of the ureteral stent when the elongate positioner is in the first position, the projection being disposed outside the opening of the ureteral stent when the elongate positioner is in the second position.

7. The assembly of claim 6, wherein the bendable portion having the projection flexes when the elongate positioner is moved between the first position and the second position.

8. The assembly of claim 6, wherein the projection extends in a direction substantially orthogonal to a longitudinal axis defined by the elongate positioner when the elongate positioner is in the first position.

9. The assembly of claim 1, wherein the lumen of the elongate positioner extends from the distal end portion of the elongate positioner to the proximal end portion of the elongate positioner, wherein the guidewire is configured to extend within the lumen of the elongate positioner from the proximal end portion of the elongate positioner to the distal end portion of the elongate positioner, the elongate positioner being in the first position when at least a portion of the guidewire is disposed within at least a portion of the lumen of the elongate positioner.

10. The assembly of claim 1, wherein the opening of the ureteral stent includes a first opening defined by the sidewall of the ureteral stent on a first location and a second opening defined by the sidewall of the ureteral stent on a second location, the second portion of the coupling mechanism includes a first bendable portion having a first projection and a second bendable portion having a second projection, the first projection at least partially extending into the first opening when in the first position, the second projection at least partially extending into the second opening when in the first position.

11. The assembly of claim 1, wherein a position of the elongate positioner with respect to the ureteral stent is substantially fixed when the elongate positioner is in the first position, the elongate positioner being able to move with respect to the ureteral stent when the elongate positioner is in the second position.

12. An assembly, comprising:
a ureteral stent having a first end portion, a second end portion opposite the first end portion, and a medial portion located between the first end portion and the second end portion, the first end portion of the ureteral stent being configured to be placed within a kidney of a patient, at least a portion of the medial portion being configured to be placed within a ureter of the patient, the ureteral stent having a sidewall, the sidewall having an inner surface and outer surface, the inner surface of the sidewall defining a lumen, the sidewall defining an opening that extends from the inner surface to the outer surface, the opening defining a first portion of a coupling mechanism, the first end portion of the ureteral stent having a retention member, the retention member having a first configuration and a second configuration, the retention member being non-linear and configured to help retain the first end portion of the ureteral stent in place within the kidney of the patient when the retention member is in the second configuration;

an elongate positioner configured to position the ureteral stent within the body, the elongate positioner having a first portion and a second portion, the elongate positioner having a second portion of the coupling mechanism coupled to the first portion of the coupling mechanism when the elongate positioner is in a first position, the second portion of the coupling mechanism at least partially extending into the opening from the inner surface of the sidewall of the ureteral stent when in the first position, the second portion of the coupling mechanism being disposed within the lumen defined by the ureteral stent and out of the opening of the ureteral stent when the elongate positioner is in a second position;

the first end portion of the ureteral stent being disposed adjacent the first portion of the elongate positioner when the elongate positioner is in the first position, the second end portion of the ureteral stent being disposed adjacent the second portion of the elongate positioner when the elongate positioner is in the first position, wherein the elongate positioner includes a sidewall having an inner surface, the inner surface of the sidewall of the elongate positioner defining a lumen, the second portion of the coupling mechanism being bendable such that portions of the inner surface of the sidewall of the elongate positioner move towards each other when moving from the first position to the second position; and a guidewire for insertion into the lumen of the elongate positioner, the coupling mechanism being configured such that the elongate positioner and the ureteral stent are coupled together in response to the guidewire being inserted into the lumen of the elongate positioner and advanced distally wherein the lumen of the ureteral stent, the coupling mechanism being configured such that the elongate positioner and the ureteral stent are decoupled in response to the guidewire being removed from the lumen of the elongate positioner by proximal advancement from inside the lumen of the ureteral stent.

13. The assembly of claim 12, wherein the second portion of the coupling mechanism includes a bendable portion defined by the sidewall of the elongate positioner, the bendable portion having a projection, the bendable portion configured to flex into the opening of the ureteral stent when in the first position.

14. The assembly of claim 12, wherein the coupling mechanism has an engaged configuration and a disengaged configuration.

15. The assembly of claim 12, wherein the elongate positioner is in the first position when the guidewire is disposed within the lumen of the elongate positioner, the elongate positioner being in the second position when the guidewire is disposed outside the lumen of the elongate positioner.

16. The assembly of claim 12, wherein the lumen of the elongate positioner extends from a distal end portion of the elongate positioner to a proximal end portion of the elongate positioner, the second portion of the coupling mechanism having a projection, the projection being disposed within the opening of the ureteral stent when the elongate positioner is in the first position, the projection being disposed outside the opening of the ureteral stent when the elongate positioner is in the second position.

17. The assembly of claim 16, wherein the projection extends in a direction substantially orthogonal to a longitudinal axis defined by the elongate positioner when the elongate positioner is in the first position.

18. The assembly of claim 12, wherein the lumen of the elongate positioner extends from a distal end portion of the elongate positioner to a proximal end portion of the elongate positioner, the second portion of the coupling mechanism having a projection having an extended configuration and a retracted configuration, the projection being in its extended configuration when the guide wire is positioned within the distal end portion of the elongate positioner.

19. A ureteral stent assembly comprising:
a ureteral stent having a distal end portion for placement in a kidney of a patient, a proximal end portion opposite the distal end portion, and a medial portion located between the distal end portion and the proximal end portion, the ureteral stent having a sidewall, the sidewall having an inner surface and outer surface, the inner surface of the sidewall defining a lumen between the distal end portion of the ureteral stent and the proximal end portion of the ureteral stent, the sidewall on the distal end portion of the ureteral stent defining an opening that extends from the inner surface to the outer surface, the opening defining a first portion of a coupling mechanism, the proximal end portion being configured to be placed in at least one of a ureter of the patient, a bladder of the patient, and outside of a body of the patient, the distal end portion of the ureteral stent having a retention member, the retention member having a first configuration and a second configuration, the retention member being non-linear and configured to help retain the distal end portion of the ureteral stent in place within the kidney of the patient when the retention member is in its second configuration;

an elongate positioner for positioning the ureteral stent in a ureter, the elongate positioner having a distal end portion for insertion into at least one of the kidney of the patient and the ureter of the patient, a proximal end portion for placement outside of the body of the patient, and a medial portion located between the distal end portion of the elongate positioner and the proximal end portion of the elongate positioner, the distal end portion of the elongate positioner having a second portion of the coupling mechanism coupled to the first portion of the coupling mechanism when the elongate positioner is in a first position, at least a portion of the elongate positioner being disposed within the lumen of the ureteral stent when in the first position, the second portion of the coupling mechanism at least partially extending into the opening from the inner surface of the sidewall of the ureteral stent when in the first position, the second portion of the coupling mechanism being disposed within the lumen defined by the ureteral stent and uncoupled from the first portion of the coupling mechanism when the elongate positioner is in a second position, wherein the elongate positioner defines a lumen extending from the proximal end portion of the elongate positioner to the distal end portion of the elongate positioner, the elongate positioner including a body portion, the second portion of the coupling mechanism extending from the body portion, the second portion of the coupling mechanism being configured to move with respect to the body portion between an extended position and a retracted position and being biased toward the retracted position; and a guidewire configured to extend within the lumen of the elongate positioner from the proximal end portion of the elongate positioner to the distal end portion of the elongate positioner, the guidewire urging the second portion of the coupling mechanism to the extended position such that the second portion of the coupling mechanism at least partially extends within the opening of the ureteral stent when at least a portion of the guidewire is disposed within at least a portion of the lumen of the elongate positioner, the coupling mechanism being configured such that the elongate positioner and the ureteral stent are coupled together in response to the guidewire being inserted into the lumen of the elongate positioner and advanced distally wherein the lumen of the ureteral stent, the coupling mechanism being configured such that the elongate positioner and the ureteral stent are decoupled in response to the guidewire being removed from the lumen of the elongate positioner by proximal advancement from inside the lumen of the ureteral stent.

20. A ureteral stent assembly comprising:
a ureteral stent having a distal end portion for placement in a kidney of a patient, a proximal end portion opposite the distal end portion, and a medial portion located between the distal end portion and the proximal end portion, the ureteral stent defining a lumen between the distal end portion of the ureteral stent and the proximal end portion of the ureteral stent, the distal end portion of the ureteral stent defining a through-hole through a sidewall of the ureteral stent, the through-hole defining a first portion of a coupling mechanism, the proximal end portion being configured to be placed in at least one of a ureter of the patient, a bladder of the patient, and outside of a body of the patient, the distal end portion of the ureteral stent having a retention member, the retention member having a first configuration and a second configuration, the retention member being non-linear and configured to help retain the distal end portion of the ureteral stent in place within a kidney of the patient when the retention member is in its second configuration;

an elongate positioner for positioning the ureteral stent in a ureter, the elongate positioner having a distal end portion for insertion into at least one of the kidney of the patient and the ureter of the patient, a proximal end portion for placement outside of the body of the patient, and a medial portion located between the distal end portion of the elongate positioner and the proximal end portion of the elongate positioner, the elongate positioner having a sidewall, the sidewall having an inner surface defining a lumen extending from the proximal end portion of the elongate positioner to the distal end portion of the elongate positioner, the distal end portion of the elongate positioner having a second portion of the coupling mechanism coupled to the first portion of the coupling mechanism when the elongate positioner is in a first position, the second portion of the coupling mechanism including a bendable portion having a projection, the bendable portion being defined by the sidewall of the elongate positioner, the projection extending away from an outer surface of the sidewall of the elongate positioner, the elongate positioner disposed within the lumen of the ureteral stent between the distal end portion of the ureteral stent and the proximal end portion of the ureteral stent when in the first position, the second portion of the coupling mechanism being uncoupled from the first portion of the coupling mechanism when the elongate positioner is in a second position, the second portion of the coupling mechanism being configured to move between an extended position and a retracted position and being biased toward the retracted position; and a guidewire configured to extend within the lumen of the elongate positioner from the proximal end portion of the elongate positioner to the distal end portion of the elongate positioner, the guidewire urging the second portion of the coupling mechanism to the extended position such that the projection at least partially extends within the through-hole of the ureteral stent when at least a portion of the guidewire is disposed within at least a portion of the lumen of the elongate positioner, the coupling mechanism being configured such that the elongate positioner and the ureteral stent are coupled together in response to the guidewire being inserted into the lumen of the elongate positioner and advanced distally wherein the lumen of the ureteral stent, the coupling mechanism being configured such that the elongate positioner and the ureteral stent are decoupled in response to the guidewire being removed from the lumen of the elongate positioner by proximal advancement from inside the lumen of the ureteral stent.

21. The assembly of claim 20, wherein the through-hole of the ureteral stent includes a first through-hole defined by the sidewall of the ureteral stent at a first location and a second through-hole defined by the sidewall of the ureteral stent at a second location, the bendable portion having the projection including a first bendable portion having a first projection and a second bendable portion having a second projection, the first projection at least partially extending into the first through-hole in the extended position, the second projection at least partially extending into the second through-hole in the extended position.

* * * * *